US009861700B2

(12) United States Patent
Andrade De Freitas et al.

(10) Patent No.: US 9,861,700 B2
(45) Date of Patent: Jan. 9, 2018

(54) NATURAL BIOCOMPOSITE POWDER PREPARED FROM PICHIA PASTORIS BIOMASS, METHOD OF PREPARATION AND ITS USE AS EXCIPIENT

(71) Applicants: Maria Filomena Andrade De Freitas, Pinhal Novo (PT); Christophe François Aimé Roca, Lisbon (PT); Fernando Miguel Da Silva Cruz, Cascais (PT); Maria D'Ascensão Carvalho Fernandes De Miranda Reis, Lisbon (PT); Inês Da Silva Farinha, Almada (PT); Bárbara Ferreira Chagas, Atouguia de Baleia (PT); Rui Manuel Freitas Oliveira, Costa da Caparica (PT)

(72) Inventors: Maria Filomena Andrade De Freitas, Pinhal Novo (PT); Christophe François Aimé Roca, Lisbon (PT); Fernando Miguel Da Silva Cruz, Cascais (PT); Maria D'Ascensão Carvalho Fernandes De Miranda Reis, Lisbon (PT); Inês Da Silva Farinha, Almada (PT); Bárbara Ferreira Chagas, Atouguia de Baleia (PT); Rui Manuel Freitas Oliveira, Costa da Caparica (PT)

(73) Assignee: Pharma73, S.A., Borba (PT)

( * ) Notice: Subject to any disclaimer, the term of this patent is extended or adjusted under 35 U.S.C. 154(b) by 484 days.

(21) Appl. No.: 13/837,828

(22) Filed: Mar. 15, 2013

(65) Prior Publication Data

US 2013/0251806 A1 Sep. 26, 2013

Related U.S. Application Data

(60) Provisional application No. 61/614,789, filed on Mar. 23, 2012.

(51) Int. Cl.
*A61K 47/36* (2006.01)
*A23L 29/269* (2016.01)

(52) U.S. Cl.
CPC ............ *A61K 47/36* (2013.01); *A23L 29/271* (2016.08)

(58) Field of Classification Search
USPC .......................................................... 424/489
See application file for complete search history.

(56) References Cited

U.S. PATENT DOCUMENTS 2,118,370 A 5/1938 Wessblad
4,992,540 A 2/1991 Jamas et al.
5,169,638 A * 12/1992 Dennis et al. ................ 424/457
5,654,007 A * 8/1997 Johnson et al. .............. 424/489
6,210,686 B1 * 4/2001 Bell ........................ A23L 1/296 424/400
8,614,070 B2 12/2013 Carvalho Fernandes De Miranda Reis et al.
8,679,796 B2 3/2014 Carvalho Fernandes De Miranda Reis et al.
2010/0003292 A1 1/2010 Gautier et al.
2010/0221382 A1 9/2010 Tiessedre
2011/0159288 A1 6/2011 Carvalho Fernandes De Miranda Reis et al.

FOREIGN PATENT DOCUMENTS

EP 2221358 A1 8/2010
GB 2259709 A 3/1993
WO WO/2003/068824 8/2003
WO WO 03068824 * 8/2003
WO WO 2004/092391 10/2004
WO WO 2006/121803 A1 11/2006
WO WO/2010/013174 2/2010
WO WO2010013174 * 7/2010
WO WO/2013/140222 9/2013

OTHER PUBLICATIONS

Gallaher (J. Nutr. Nov. 1, 2000 vol. 130 No. 11 2753-2759).*
Zacour (J. Nutr. Sci. Vitaminol., 38, 609-613, 1992).*
Mohammed (Food Hydrocolloids 31 (2013) 166e171).*
Sigma (http://www.sigmaaldrich.com/catalog/product/sigma/89862?lang=en®ion=US; accessed Dec. 27, 2014).*
Jul. 1, 2013 International Search Report issued in connection with PCT International Application No. PCT/IB2013/000403.
Jul. 1, 2013 Written Opinion of the International Searching Authority issued in connection with PCT International Application No. PCT/IB2013/000403.
Jun. 25, 2013 Office Action issued in connection with Canadian Patent Application No. 2,809,279.
Aug. 22, 2013 Amendment in Response to Jun. 25, 2013 Office Action in connection with Canadian Patent Application No. 2,809,279.
Sep. 20, 2013 Office Action issued in connection with Canadian Patent Application No. 2,809,279.
Oct. 21, 2013 Amendment in Response to Sep. 20, 2013. Office Action in connection with Canadian Patent Application No. 2,809,279.
Nov. 13, 2013 Voluntary Amendment in connection with Canadian Patent Application No. 2,809,279.

(Continued)

*Primary Examiner* — Devang K Thakor
(74) *Attorney, Agent, or Firm* — Gary J. Gershik; Cooper & Dunham LLP

(57) ABSTRACT

The present invention concerns a natural biocomposite powder prepared from the biomass of yeast *Pichia pastoris*, comprising chitin-glucan complex (CGC) and mannose-containing polysaccharides. In a second aspect, the invention concerns the method of preparation of the natural biocomposite powder. The invention also concerns the method to obtain *Pichia pastoris* biomass with increased CGC content, as well as increased chitin to glucan content in the CGC. Finally, the invention concerns the use of the natural biocomposite powder, prepared from the cell wall of yeast *Pichia pastoris* by the method according to the invention, as excipient in the pharmaceutical, cosmetics or food industries.

16 Claims, 1 Drawing Sheet

(56) References Cited

OTHER PUBLICATIONS

Nov. 21, 2013 Notice of Allowance in connection with Canadian Patent Application No. 2,809,279.

Chagas B et al: "Production of chitin-glucan complex (CGC) from biodiesel industry byproduct," Journal of Biotechnology, vol. 150, Nov. 1, 2010 (Nov. 1, 2010), pp. 381-382.

Bays et al., Chitin-glucan fiber effects on oxidized low-density lipoprotein: a randomized controlled trial. European journal of clinical nutrition. Jan. 1, 2013;67(1):2-7.

Communication pursuant to Article 94(3) EPC dated Oct. 2, 2015 in connection with European Patent Application No. 13721 379.9.

Response to Communication pursuant to Article 94(3) EPC dated Jan. 28, 2016 in connection with European Patent Application No. 13721 379.9.

First Office Action dated May 3, 2016 in connection with Chinese Patent Application 201380016117.2 including English.

Response to First Office Action dated Sep. 19, 2016 in connection with Chinese Patent Application 201380016117.2.

Jul. 3, 2012 Office Action issued in connection with U.S. Appl. No. 13/056,902.

Jan. 3, 2013 Amendment in Response to Jul. 3, 2012 Office Action submitted in connection with U.S. Appl. No. 13/056,902.

Apr. 5, 2013 Final Office Action issued in connection with U.S. Appl. No. 13/056,902.

Jun. 3, 2013 Amendment in Response to Apr. 5, 2013 Final Office Action submitted in connection with U.S. Appl. No. 13/056,902.

Jun. 18, 2013 Advisory Action issued in connection with U.S. Appl. No. 13/056,902.

Jul. 25, 2013 Amendment in Response to Jun. 18, 2013 Advisory Action and Apr. 5, 2013 Final Office Action submitted in connection with U.S. Appl. No. 13/056,902.

Aug. 19, 2013 Notice of Allowance issued in connection with U.S. Appl. No. 13/056,902.

Celik et al., "Use of Biodiesel Byproduct Crude Glycerol as the Carbon Source for Fermentation Processes by Recombinant Pichia pastoris." *Ind. Eng. Res.* 47:2985-2990. Published on Web Apr. 3, 2008.

Kishore D. Rane et al.; "Production of Chitosan by Fungi"; *Food Biotechnology* (New York), vol. 7,No. 1, 1993, pp. 11-33.

Ivshin et al.; "Methods for Isolation of Chitin-Glucan Complexes from Higher Fungi Native Biomass"; Polymer Sciences, vol. 49, No. 11-12,2007, pp. 305-310.

M. Beran et al. "Isolation and Some Applications of Fungal Chitin-Glucan Complex and Chitosan" 2004.

Jozef Synowiecki et al. "Production, Properties, and Some New Applications of Chitin and Its Derivatives" *Critical Reviews in Food Science and Nutrition*, vol. 43, No. 2, Mar. 2003, pp. 145-171.

Chagas et al.; "Extraction and Purification of Cell Wall Polysaccharides from Pichia Pastoris Biomass" *New Biotechnology*, vol. 25, Sep. 1, 2009, p. S214.

International Search Report for PCT/IB2009/053189 dated Mar. 10, 2010.

Invitrogen (Pichia Fermentation Process Guidelines. 2002:1-11).

Nov. 26, 2016 International Search Report issued in connection with PCT International Application No. PCT/IB2015/000708.

Nov. 26, 2016 Written Opinion of the International Searching Authority issued in connection with PCT International Application No. PCT/IB2015/000708.

Christophe Roca, et al.; "Production of yeast chitin-glucan complex from biodiesel industry byproduct"; Process Biochemistry; 2012; pp. 1670-1675; 47; Elsevier.

* cited by examiner

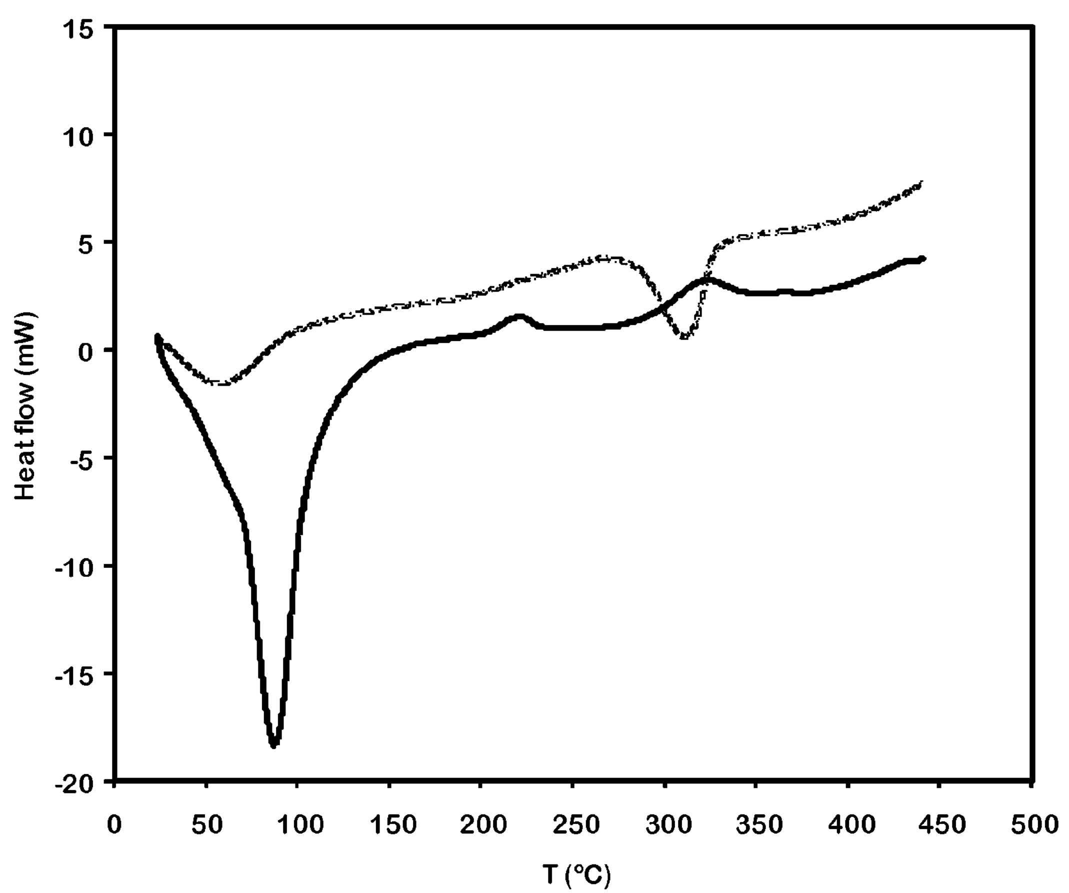
15
10
5
0
-5
-10
-15
-20
Heat flow (mW)
0
50
100
150
200
250
300
350
400
450
500
T (°C)

NATURAL BIOCOMPOSITE POWDER PREPARED FROM PICHIA PASTORIS BIOMASS, METHOD OF PREPARATION AND ITS USE AS EXCIPIENT

This application claims the benefit of U.S. Provisional Application No. 61/614,789, filed Mar. 23, 2012, the contents of which are hereby incorporated by reference.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

FIELD OF INVENTION

The present invention concerns a natural biocomposite powder prepared from the biomass of the yeast *Pichia pastoris*, comprising chitin-glucan complex (CGC) and mannose-containing polysaccharides, the method of preparation of the natural biocomposite powder, the method to obtain *Pichia pastoris* biomass with increased CGC content and increased chitin to glucan content in the CGC, and the use of the natural biocomposite powder as excipient in the pharmaceutical, cosmetics or food industries. According to the method of the invention, the obtained natural biocomposite powder offers high advantages as unique additive that can be used as a multifunctional excipient in the pharmaceutical industry (as binder, disintegrant and/or lubricant).

BACKGROUND OF THE INVENTION

The yeast cell wall is a complex network of different macromolecules, wherein polysaccharides represent the main fraction accounting for over 50% of the cells' dry weight. Mannose- and glucose-containing polysaccharides are the major components of the yeast cell wall, with lower amounts of chitin that is usually present in the form of a chitin-glucan complex. Chitin-glucan complex (CGC) is comprised of chitin (a polymer of N-acetylglucosamine units) covalently linked to β-1,3-glucans (polymer of glucose units). This copolymer has an important structural function in the yeast cell and is water insoluble. Mannose- and glucose-containing polysaccharides include mannans (polymer of mannose units), glucans (polymer of glucose units), glucomannans (polymer of mannose and glucose units) and/or galactomannans (polymer of mannose and galactose units).

Due to its composition, the yeast cell wall is a valuable source of different types of polysaccharides, including mannans, glucomannans, galactomannans, glucans, chitin and chitin-glucan complex. Polysaccharides with similar composition can also be extracted from algae, plants or animals, such as, for example, carrageenan, guar gum and chitin. However, extraction of the polysaccharides from such higher organisms (algae, plants or animals) presents many constraints: they are dependent on seasonal production, with highly variable quality and quantity, making production process particularly irreproducible. In the case of extraction of chitin from crustaceous, the resulting products can contain toxins or allergens that render them unsuitable for human uses. On the other hand, extraction from yeasts, cultivated under controlled conditions, is far more reliable, sustainable and safe.

Recently, U.S. Pat. No. 7,556,946 and Patent application US 2010/0221382, US 2010/0003292 and WO 2010/013174 disclose methods for the preparation of cell wall derivatives from fungal or yeast biomass to obtain chitin polymers or chitin-glucan polymers.

However, the methods are focused on the production of mostly chitin- and chitosan-rich polymers, without taking advantage of the presence of other polysaccharides such as mannans, glucomannans and galactomannans.

On the other hand, other documents, such as, for example, U.S. Pat. No. 6,444,448 and Patent Applications EP 2272876 and WO 2010/070207, disclose methods for obtaining glucans and mannans from different natural sources, including bacteria, fungi, yeast and plants. Such methods rely on enzymatic (EP 2272876) or autolytic (U.S. Pat. No. 6,444,448) treatments, or on a combination of acid and alkaline treatments (2010/070207).

Excipients are ingredients used by the pharmaceutical industry to formulate active ingredients into finished dosage forms. Formulation of active pharmaceutical ingredients (APIs) with excipients is primordial to ensure an efficient drug delivery with the desired properties, together with a robust manufacturing process. Essentially, excipients are used to provide a matrix in which the drug can be handled to control the rate of dosage, to aid in the processing of the drug delivery system during its manufacture and assist in product identification, protect, support or enhance stability, bioavailability or patient acceptability, and to enhance any other attribute of the overall safety, effectiveness or delivery of the drug during storage or use.

The principal categories of excipients are binders and fillers, disintegrants, diluents, lubricants and glidants, preservatives and antioxidants. Ranging from 15% to 99% of the total weight of a given drug, excipients are extremely relevant for the drug production process, in terms of procurement, logistics, quality control and process productivity. Consequently, excipients must be able to deliver high-functionality advantages to the formulator, such as increased lubricity, improved flowability, enhanced compressibility and compatibility, improved product characteristics and sustainable production process.

As an example, the preparation of tablet dosage forms with acceptable physicochemical properties involves the use of fillers, binders, glidants and lubricants, mentioned above. In order to be compressed into tablets, such materials must have specific physical properties, namely, they must be free flowing, cohesive and lubricated. Moreover, for the release of the active pharmaceutical ingredient, a disintegrant is added to facilitate the breakup of the solid dosage form.

Although the traditional tablet components have long-established efficacy, some of them have disadvantages that are related to their cost, moderate efficiency and often time consuming excipients processes. Hence, there is a need for new excipient formulations that overcome these disadvantages. One great advantage would be the possibility of using a high functionally excipient that combines in itself the properties of different traditional excipient components, thus making the formulation process easier and faster.

Currently, most traditional excipients are synthesized or chemically modified using natural molecules as starting points. Cellulose or starch derivatives, synthetic polymers and alcohols are just a few examples that a person skilled in the art will easily identify. The use of entirely natural excipients in the pharmaceutical industry remains limited. However, these natural excipients have the advantage of being safe, non-toxic, biocompatible and biodegradable. In view of this, natural polysaccharides can be used for the development of versatile excipients with improved properties. They can be extracted from various origins, such as plants, animals or even microorganisms.

Among the natural polysaccharides emerging today as excipients, people skilled in the art will identify polymers, such as guar gum or carrageenans. Guar gum, used as thickener for lotions and creams, as a tablet binder or as an emulsion stabilizer, is a galactomannan (polymer of galactose and mannose units), which occurs as a storage polysaccharide in the seed endosperm of some plants. Carrageenans are the generic name for a family of high molecular weight sulphated polysaccharides obtained from certain species of red seaweeds, suitable for tablet manufacturing.

GENERAL DESCRIPTION OF THE INVENTION

This invention concerns a natural biocomposite powder prepared from the cell wall of yeast *Pichia pastoris* comprising chitin-glucan complex and mannose-containing polysaccharides.

This invention also concerns the use of this natural biocomposite powder, prepared from the cell wall of *Pichia pastoris* yeast by the method according to the invention, as excipients for the pharmaceutical industry.

Moreover, the invention concerns the preparation method of the natural biocomposite powder of the invention, which includes the procedure for producing *P. pastoris* biomass, extracting polysaccharides from *P. pastoris* biomass that result in the natural biocomposite of the present invention, as well as the procedures for drying and milling the natural biocomposite to obtain the desired powder.

According to the method of the invention, the amount of CGC and mannose-containing polysaccharides in the natural biocomposite are adjusted by controlling the conditions of the procedures for extracting the natural biocomposite from *P. pastoris* cell wall. The physical properties of the natural biocomposite powder, namely, bulk density, particle size distribution and moisture, are modulated by controlling the conditions for drying and milling the natural biocomposite.

The invention also concerns the cultivation conditions to obtain *P. pastoris* biomass with specific CGC content, as well as specific chitin to glucan ratio.

Aspects of the present invention relate to a biocomposite powder comprising 20-95% (w/w) chitin-glucan complex (CGC), preferably 40-90% (w/w), and up to 50% mannose-containing polysaccharides, preferably up to 25% (w/w), extracted from the biomass of the yeast *Pichia pastoris*, wherein the size of particles of the biocomposite powder range between 5 and 1500 μm, preferably between 30 and 400 μm, and wherein the apparent bulk density of the biocomposite powder being between 0.05 and 1.0 g/cm$^3$, preferably between 0.5 and 1.0 g/cm$^3$.

Aspects of the present invention relate to a method of preparation of a biocomposite powder comprising polysaccharides extracted from the biomass of the yeast *Pichia pastoris* according to the present invention, characterized by the following sequential steps:

a) contacting *P. pastoris* biomass with an alkaline aqueous solution (NaOH, KOH, $Ca(OH)_2$, $Na_2CO_3$, $K_2CO_3$, $CaCO_3$, $NaHCO_3$ or $KHCO_3$, preferably NaOH or $NaHCO_3$), at a concentration between 0.5 and 5.0 M, wherein the biomass is in suspension, preferably at a concentration between 10 and 15% (w/v);

b) stirring the alkaline biomass suspension at a temperature between 60-90° C. for a period of 1-5 hours to form a reaction mixture;

c) cooling the reaction mixture to a temperature between 30 and 45° C., and after cooling, separating the alkaline insoluble fraction in the reaction mixture from the soluble fraction by centrifugation or filtration;

d) washing the alkaline insoluble fraction with one or several of the following solvent systems to for a slurry:
   i. Water,
   ii. Aqueous saline solution, such as, for example, phosphate buffer saline solution (PBS) (20.45 g/L NaCl; 0.46 g/L KCl; 10.14 g/L $Na_2HPO_4.7H_2O$; 0.54 g/L $KH_2PO_4$, pH 7.2),
   iii. Ethanol (70%, v/v), or iv. Aqueous solution of an acid, such as, for example, hydrochloric acid (HCl);

e) drying the slurry using one of the following procedures:
   i. Freezing with liquid nitrogen, followed by lyophilization;
   ii. Drying in an oven at a temperature between 60 and 80° C., during 12-18 hours;
   iii. Spray-drying at a temperature of between 120 and 200° C., during a period of time between 1 and 10 seconds, preferably at a temperature between 130 and 150° C.; or
   iv. Fluidized bed drying with inlet air between 70° C. and 90° C.;

f) milling the dried material to obtain a powder by passing it one or more times through a Comminuting Mill, a Cone Mill, a Ball Mill, a Multi Mill or a Roller Compactor, equipped with sieves ranging from 0.25 to 10 mm in the output, operated with rotor speeds between 500 and 5000 rpm; and g) calibrating the powder by passing it one or more times through an oscillating and rotating sieve mill equipped with sieves ranging from 0.05 to 1.5 mm.

DESCRIPTION OF THE DRAWINGS

FIG. 1—DSC scans of high-mannose content (full line) and low-mannose content (dashed line) biocomposites prepared from *P. pastoris* biomass.

DETAILED DESCRIPTION OF THE INVENTION

Aspects of the present invention relate to a biocomposite powder comprising 20-95%, or about 20, 30, 40, 50, 60, 70, 80, 90, or 95% (w/w) chitin-glucan complex (CGC), preferably 40-90% (w/w), and up to about 50% mannose-containing polysaccharides, preferably up to about 25, 30, 35, 40, or 45% (w/w), extracted from the biomass of the yeast *Pichia pastoris*, wherein the size of particles of the biocomposite powder range between 5 and 1500 μm, preferably between 30 and 400 μm, or about 50, 100, 150, 200, 250, 300, or 350 μm, and wherein the apparent bulk density of the biocomposite powder being between 0.05 and 1.0 g/cm$^3$, preferably between 0.5 and 1.0 g/cm$^3$, or about 0.5, 0.6, 0.7, 0.8, 0.9, or 1.0 g/cm$^3$.

In some embodiments, the granulometric distribution of the biocomposite powder is such that about 90% of the particles have a size below 355 μm, about 50% have a size below 250 μm and less than about 10% have a size below 90 μm.

In some embodiments, the ratio of chitin to glucan in the CGC is up to 15 to 90 (% mol), preferably higher than 15 to 85 (% mol), more preferably higher than 50 to 50 (% mol).

Aspects of the present invention relate to a method of preparation of a biocomposite powder comprising polysaccharides extracted from the biomass of the yeast *Pichia*

*pastoris* according to the present invention, characterized by the following sequential steps:

a) contacting *P. pastoris* biomass with an alkaline aqueous solution, at a concentration between 0.5 and 5.0 M, or about 1.0, 1.5, 2.0, 2.5, 3.0, 3.5, 4.0, 4.5 or 5.0M, wherein the biomass is in suspension, preferably at a concentration between 10 and 15%, or about 11, 12, 13, 14, or 15 (w/v);

b) stirring the alkaline biomass suspension at a temperature between about 60-90° C. for a period of about 1-5 hours to form a reaction mixture;

c) cooling the reaction mixture to a temperature between about 30 and 45° C., and after cooling, separating the alkaline insoluble fraction in the reaction mixture from the soluble fraction by centrifugation or filtration;

d) washing the alkaline insoluble fraction with one or several of the following solvent systems to form a slurry:
   i. water,
   ii. aqueous saline solution,
   iii. ethanol (about 70%, v/v), or
   iv. aqueous solution of an acid;

e) drying the slurry using one of the following procedures:
   i. freezing with liquid nitrogen, followed by lyophilization;
   ii. drying in an oven at a temperature between about 60 and 80° C., for about 12-18 hours;
   iii. spray-drying at a temperature of between about 120 and 200° C. or about 130, 140, 150, 160, 170, 180, or 190° C., for a period of time between about 1 and 10 seconds; or
   iv. fluidized bed drying with inlet air between about 70° C. and 90° C.;

f) milling the dried material to obtain a powder by passing it one or more times through a Comminuting Mill, a Cone Mill, a Ball Mill, a Multi Mill or a Roller Compactor, equipped with sieves ranging from about 0.25 to 10 mm in the output, operated with rotor speeds between about 500 and 5000 rpm, or about 600, 700, 800, 900, 1000, 2000, 3000, 4000, or 5000 rpm; and g) calibrating the powder by passing it one or more times through an oscillating and rotating sieve mill equipped with sieves ranging from about 0.05 to 1.5 mm.

In some embodiments, *Pichia pastoris* biomass is obtained with a CGC content up to about 15% (w/w), by cultivation in standard basal salts medium (BSM) supplemented with glycerol, sorbitol, glucose, fructose, galactose, xylose, sucrose, lactose, mixtures thereof or materials containing such compounds as carbon sources at a concentration between 30 and 60 g/L, preferably between about 40 and 50 g/L, under batch, fed-batch or continuous mode, with controlled temperature at about 28-32° C., controlled pH at about 4.5-5.5, and controlled dissolved oxygen concentration (DO) above about 10, 20, 30, 40, or 50%, preferably above about 30%, more preferably above about 50%.

In some embodiments, *Pichia pastoris* biomass is obtained with a CGC content above about 15% (w/w), by cultivation in BSM supplemented with glycerol, glucose, fructose, galactose, xylose, sucrose, lactose, mixtures thereof or materials containing such compounds as carbon sources at concentrations between about 60 and 180 g/L, preferably between about 80 and 120 g/L.

In some embodiments, *Pichia pastoris* biomass is obtained with a CGC content above about 15% (w/w), by cultivation without temperature control.

In some embodiments, *Pichia pastoris* biomass is obtained with a CGC content above 15% (w/w), by cultivation with controlled temperature at about 28-32° C. until the stationary growth phase is reached and then increasing the temperature by about 5-20° C., preferably by about 10-15° C., during about 2-48 hours, preferably during about 6-24 hours.

In some embodiments, *Pichia pastoris* biomass is obtained with a CGC content above about 15% (w/w), by cultivation without pH control.

In some embodiments, *Pichia pastoris* biomass is obtained with a CGC content above about 15% (w/w), by cultivation with controlled pH at about 3.5-6.5, or about 3.5, 4.0, 5.0, 5.5, 6.0, or 6.5, until the stationary growth phase is reached and then increasing the pH by about 1.0-3.0, preferably by about 2.0-3.0, during or over a period of about 2-48 hours or 6, 12, 18, 24, 36, or 48 hours, preferably during or over a period of 6-24 hours.

In some embodiments, *Pichia pastoris* biomass is obtained with a CGC content above about 15% (w/w), by cultivation in BSM supplemented with caffeine or materials containing caffeine, being the final concentration of caffeine in BSM up to about 100 mmol/L, preferably between about 10-50 mmol/L.

In some embodiments, *Pichia pastoris* biomass is obtained with a CGC content above about 15% (w/w), by cultivation in BSM supplemented with glucosamine at a concentration up to about 100 mmol/L, preferably between about 10-50 mmol/L.

In some embodiments, *Pichia pastoris* biomass is obtained with a CGC content above about 15% (w/w), by cultivation in BSM supplemented with a surfactant, such as SDS, Triton X100 or PEG, at a concentration up to about 1.0% (w/v), preferably between about 0.01 and 0.1% (w/v).

In some embodiments, *Pichia pastoris* biomass is obtained with a CGC content above about 15% (w/w), by cultivation in BSM supplemented with calcium, cobalt, copper, iron, magnesium and/or manganese in the form of chloride, sulphate and/or phosphate salts at concentrations between about 1 and 200 mmol/L, or about 5, 10, 15, 20, 25, 30, 35, 40, 45, or 50 mmol/L, preferably between about 5 and 50 mmol/L.

In some embodiments, the ratio of chitin to glucan in the CGC is above about 15 to 85 (% mol), preferably above about 50 to 50 (% mol) by cultivation of *Pichia pastoris* in BSM supplemented with glucose, sucrose, lactose, mixtures thereof or materials containing such compounds as carbon sources at concentrations between about 40 and 180 g/L, or about 40, 50, 60, 70, 80, 90, 100, 120, 140, 160, or 180 g/L preferably between about 60 and 120 g/L.

In some embodiments, the ratio of chitin to glucan in the CGC is above about 15 to 85 (% mol), preferably above about 50 to 50 (% mol) by cultivation of *Pichia pastoris* in BSM supplemented with caffeine or materials containing caffeine, being the final concentration of caffeine in the BSM up to about 100 mmol/L, or about 10, 15, 20, 25, 30, 35, 40, 45, or 50 mmol/L, preferably between 10-50 mmol/L.

In some embodiments, the ratio of chitin to glucan in the CGC is above about 15 to 85 (% mol), preferably above about 50 to (% mol) by cultivation of *Pichia pastoris* in BSM supplemented with glucosamine at a concentration up to about 100 mmol/L, or about 10, 15, 20, 25, 30, 35, 40, 45, or 50 mmol/L, preferably between about 10-50 mmol/L.

In some embodiments, the ratio of chitin to glucan in the CGC is above about 15 to 85 (% mol), preferably above 50 to 50 (% mol) by cultivation of *Pichia pastoris* with pH above about 6.5.

In some embodiments, *Pichia pastoris* biomass is obtained as a pharmaceutical industry byproduct.

Aspects of the present invention relate to a biocomposite powder comprising 20-95% (w/w) chitin-glucan complex (CGC), and up to 50% mannose-containing polysaccharides, extracted from the biomass of the yeast *Pichia pastoris*, wherein the size of particles of the biocomposite powder range between 5 and 1500 μm, and wherein the apparent bulk density of the biocomposite powder is between 0.05 and 1.0 g/cm$^3$.

In some embodiments, the biocomposite powder comprises up to 25% (w/w) mannose-containing polysaccharides.

In some embodiments, the size of particles of the composite powder range between 30 and 400 μm.

In some embodiments, the apparent bulk density of the biocomposite powder is between 0.5 and 1.0 g/cm$^3$.

In some embodiments, the granulometric distribution of the biocomposite powder is such that 90% of the particles have a size below 355 μm, 50% have a size below 250 μm and less than 10% have a size below 90 μm.

In some embodiments, the ratio of chitin to glucan in the CGC is up to 15 to 90 (% mol).

In some embodiments, the ratio of chitin to glucan in the CGC is higher than 15 to 85 (% mol)

In some embodiments, the ratio of chitin to glucan in the CGC is higher than 50 to 50 (% mol).

Aspects of the present invention relate to a method of preparation of a biocomposite powder comprising polysaccharides extracted from the biomass of the yeast *Pichia pastoris* according to the present invention, characterized by the following sequential steps:

a) contacting *P. pastoris* biomass with an alkaline aqueous solution, at a concentration between 0.5 and 5.0 M, wherein the biomass is in suspension, preferably at a concentration between 10 and 15% (w/v);
b) stirring the alkaline biomass suspension at a temperature between 60-90° C. for a period of 1-5 hours to form a reaction mixture;
c) cooling the reaction mixture to a temperature between 30 and 45° C., and after cooling, separating the alkaline insoluble fraction in the reaction mixture from the soluble fraction by centrifugation or filtration;
d) washing the alkaline insoluble fraction with one or several of the following solvent systems to form a slurry:
   i. water,
   ii. aqueous saline solution,
   iii. ethanol (70%, v/v), or
   iv. aqueous solution of an acid;
e) drying the slurry using one of the following procedures:
   v. freezing with liquid nitrogen, followed by lyophilization;
   vi. drying in an oven at a temperature between 60 and 80° C., for 12-18 hours;
   vii. spray-drying at a temperature of between 120 and 200° C., for a period of time between 1 and 10 seconds; or
   viii. fluidized bed drying with inlet air between 70° C. and 90° C.;
f) milling the dried material to obtain a powder by passing it one or more times through a Comminuting Mill, a Cone Mill, a Ball Mill, a Multi Mill or a Roller Compactor, equipped with sieves ranging from 0.25 to 10 mm in the output, operated with rotor speeds between 500 and 5000 rpm; and
g) calibrating the powder by passing it one or more times through an oscillating and rotating sieve mill equipped with sieves ranging from 0.05 to 1.5 mm.

In some embodiments, the aqueous alkaline solution is NaOH, KOH, $Ca(OH)_2$, $Na_2CO_3$, $K_2CO_3$, $CaCO_3$, $NaHCO_3$ or $KHCO_3$.

In some embodiments, the aqueous alkaline solution is NaOH or $NaHCO_3$.

In some embodiments, the aqueous solution in step d) ii) is phosphate buffer saline solution (PBS) (20.45 g/L NaCl; 0.46 g/L KCl; 10.14 g/L $Na_2HPO_4.7H_2O$; 0.54 g/L $KH_2PO_4$, pH 7.2).

In some embodiments, the aqueous solution of an acid in step d) iv) is an aqueous solution of hydrochloric acid (HCl).

In some embodiments, the spray-drying is at a temperature between 130 and 150° C.

In some embodiments, the *Pichia pastoris* biomass is obtained with a CGC content up to 15% (w/w), by cultivation in standard basal salts medium (BSM) supplemented with glycerol, sorbitol, glucose, fructose, galactose, xylose, sucrose, lactose, mixtures thereof or materials containing such compounds as carbon sources at a concentration between 30 and 60 g/L, under batch, fed-batch or continuous mode, with the temperature controlled to be 28-32° C., the pH controlled to be 4.5-5.5, and with the dissolved oxygen concentration (DO) controlled to be above 10%.

In some embodiments, the dissolved oxygen concentration (DO) is controlled to be above 30%.

In some embodiments, the dissolved oxygen concentration (DO) is controlled to be above 50%.

In some embodiments, the *Pichia pastoris* biomass is obtained with a CGC content up to 15% (w/w), by cultivation in standard basal salts medium (BSM) supplemented with glycerol, sorbitol, glucose, fructose, galactose, xylose, sucrose, lactose, mixtures thereof or materials containing such compounds as carbon sources at a concentration between 40 and 50 g/L.

In some embodiments, the *Pichia pastoris* biomass is obtained with a CGC content above 15% (w/w), by cultivation in BSM supplemented with glycerol, glucose, fructose, galactose, xylose, sucrose, lactose, mixtures thereof or materials containing such compounds as carbon sources at concentrations between 60 and 180 g/L.

In some embodiments, the *Pichia pastoris* biomass is obtained with a CGC content above 15% (w/w), by cultivation in BSM supplemented with glycerol, glucose, fructose, galactose, xylose, sucrose, lactose, mixtures thereof or materials containing such compounds as carbon sources at concentrations between 80 and 120 g/L.

In some embodiments, *Pichia pastoris* biomass is obtained with a CGC content above 15% (w/w), by cultivation without temperature control.

In some embodiments, *Pichia pastoris* biomass is obtained with a CGC content above 15% (w/w), by cultivation with controlled temperature at 28-32° C. until the stationary growth phase is reached and then increasing the temperature by 5-20° C. during 2-48 hours.

In some embodiments, the *Pichia pastoris* biomass is obtained with a CGC content above 15% (w/w), by cultivation with controlled temperature at 28-32° C. until the stationary growth phase is reached and then increasing the temperature by 10-15° C., during 2-48 hours.

In some embodiments, then the stationary growth phase is reached the temperature is increased during 6-24 hours.

In some embodiments, the *Pichia pastoris* biomass is obtained with a CGC content above 15% (w/w), by cultivation without pH control.

In some embodiments, the *Pichia pastoris* biomass is obtained with a CGC content above 15% (w/w), by cultivation with controlled pH at 3.5-6.5 until the stationary growth phase is reached and then increasing the pH by 1.0-3.0 during 2-48 hours.

In some embodiments, the *Pichia pastoris* biomass is obtained with a CGC content above 15% (w/w), by cultivation with controlled pH at 3.5-6.5 until the stationary growth phase is reached and then increasing the pH by 2.0-3.0, during 2-48 hours.

In some embodiments, when the stationary growth phase is reached, the pH is increased during 6-24 hours.

In some embodiments, the *Pichia pastoris* biomass is obtained with a CGC content above 15% (w/w), by cultivation in BSM supplemented with caffeine or materials containing caffeine, wherein the final concentration of caffeine in BSM is up to 100 mmol/L.

In some embodiments, the *Pichia pastoris* biomass is obtained with a CGC content above 15% (w/w), by cultivation in BSM supplemented with caffeine or materials containing caffeine, wherein the final concentration of caffeine in BSM is between 10-50 mmol/L.

In some embodiments, the *Pichia pastoris* biomass is obtained with a CGC content above 15% (w/w), by cultivation in BSM supplemented with glucosamine at a concentration up to 100 mmol/L. preferably between 10-50 mmol/L.

In some embodiments, the *Pichia pastoris* biomass is obtained with a CGC content above 15% (w/w), by cultivation in BSM supplemented with glucosamine at a concentration between 10-50 mmol/L.

In some embodiments, the *Pichia pastoris* biomass is obtained with a CGC content above 15% (w/w), by cultivation in BSM supplemented with a surfactant, such as SDS, Triton X100 or PEG, at a concentration up to 1.0% (w/v).

In some embodiments, the *Pichia pastoris* biomass is obtained with a CGC content above 15% (w/w), by cultivation in BSM supplemented with a surfactant, such as SDS, Triton X100 or PEG, at a concentration between 0.01 and 0.1% (w/v).

In some embodiments, the *Pichia pastoris* biomass is obtained with a CGC content above 15% (w/w), by cultivation in BSM supplemented with calcium, cobalt, copper, iron, magnesium and/or manganese in the form of chloride, sulphate and/or phosphate salts at concentrations between 1 and 200 mmol/L.

In some embodiments, the *Pichia pastoris* biomass is obtained with a CGC content above 15% (w/w), by cultivation in BSM supplemented with calcium, cobalt, copper, iron, magnesium and/or manganese in the form of chloride, sulphate and/or phosphate salts at concentrations between 5 and 50 mmol/L.

In some embodiments, the ratio of chitin to glucan in the CGC is above 15 to 85 (% mol) by cultivation of *Pichia pastoris* in BSM supplemented with glucose, sucrose, lactose, mixtures thereof or materials containing such compounds as carbon sources at concentrations between 40 and 180 g/L.

In some embodiments, the ratio of chitin to glucan in the CGC is above 15 to 85 (% mol) by cultivation of *Pichia pastoris* in BSM supplemented with glucose, sucrose, lactose, mixtures thereof or materials containing such compounds as carbon sources at concentrations between 60 and 120 g/L.

In some embodiments, the ratio of chitin to glucan in the CGC is above 50 to 50 (% mol) by cultivation of *Pichia pastoris* in BSM supplemented with glucose, sucrose, lactose, mixtures thereof or materials containing such compounds as carbon sources at concentrations between 40 and 180 g/L.

In some embodiments, the ratio of chitin to glucan in the CGC is above 50 to 50 (% mol) by cultivation of *Pichia pastoris* in BSM supplemented with glucose, sucrose, lactose, mixtures thereof or materials containing such compounds as carbon sources at concentrations between 60 and 120 g/L.

In some embodiments, the ratio of chitin to glucan in the CGC is above 15 to 85 (% mol) by cultivation of *Pichia pastoris* in BSM supplemented with caffeine or materials containing caffeine, being the final concentration of caffeine in the BSM up to 100 mmol/L.

In some embodiments, the ratio of chitin to glucan in the CGC is above 15 to 85 (% mol) by cultivation of *Pichia pastoris* in BSM supplemented with glucosamine at a concentration between 10-50 mmol/L.

In some embodiments, the ratio of chitin to glucan in the CGC is above 50 to 50 (% mol) by cultivation of *Pichia pastoris* in BSM supplemented with caffeine or materials containing caffeine, being the final concentration of caffeine in the BSM up to 100 mmol/L.

In some embodiments, the ratio of chitin to glucan in the CGC is above 50 to 50 (% mol) by cultivation of *Pichia pastoris* in BSM supplemented with glucosamine at a concentration between 10-50 mmol/L.

In some embodiments, the ratio of chitin to glucan in the CGC is above 15 to 85 (% mol) by cultivation of *Pichia pastoris* with pH above 6.5.

In some embodiments, the ratio of chitin to glucan in the CGC is above 50 to 50 (% mol) by cultivation of *Pichia pastoris* with pH above 6.5.

In some embodiments, the *Pichia pastoris* biomass is obtained as a pharmaceutical industry byproduct.

Aspects of the present invention relate to the use of the biocomposite powder comprising CGC and mannose-containing polysaccharides extracted from the biomass of yeast *Pichia pastoris*, according to the present invention, as a pharmaceutical excipient.

Aspects of the present invention relate to the use of the powder comprising polysaccharides extracted from the biomass of yeast *Pichia pastoris*, according to the present invention, as a cosmetic excipient.

Aspects of the present invention relate to the use of the powder comprising polysaccharides extracted from the biomass of yeast *Pichia pastoris*, according to the present invention, in pharmaceutical formulations.

Aspects of the present invention relate to the use of the powder comprising polysaccharides extracted from the biomass of yeast *Pichia pastoris*, according to the present invention, in cosmetic formulations.

Aspects of the present invention relate to the use of the powder comprising polysaccharides extracted from the biomass of yeast *Pichia pastoris*, according to embodiments of the present invention, in food formulations.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, “0.2-5 mg/kg/day” is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

As used herein, "about" in the context of a numerical value or range means ±10% of the numerical value or range recited or claimed, unless the context requires a more limited range.

1. Characterization of the Natural Biocomposite Powder

In one embodiment, this invention concerns a natural biocomposite powder prepared from the cell wall of yeast *Pichia pastoris* comprising 20-95% (w/w) CGC, preferably 40-90% (w/w), and up to 50% (w/w) mannose-containing polysaccharides, preferably up to 25% (w/w), with particle sizes ranging between 5 and 1500 μm, preferably between 30 and 400 μm, apparent bulk densities between 0.05 and 1.0 g/cm$^3$, preferably between 0.5 and 1.0 g/cm$^3$, and sphericity coefficient ranging between 0.20 and 0.95.

The biocomposite powder preferably has a granulometric distribution such that 90% of the particles have a size below 355 μm, 50% have a size below 250 μm and less than 10% have a size below 90 μm.

The biocomposite powder comprises CGC wherein the ratio of chitin to glucan is up to 15 to 90 (% mol), preferably higher than 15 to 85 (% mol), more preferably higher than 50 to 50 (% mol).

The physical and chemical properties of the natural biocomposite powder can be adjusted in a controlled way by changing the operating parameters of one or more of the procedures of the method of the invention, namely, the procedures for producing *P. pastoris* biomass, extracting the biocomposite from *P. pastoris* cell wall, and drying and milling the natural biocomposite.

2. Method for Preparation of the Natural Biocomposite Powder From *Pichia pastoris* Biomass 2.1. Procedure for Production of *Pichia pastoris* Biomass with a CGC Content Up to 15% (w/w)

*P. pastoris* biomass is obtained with a CGC content up to 15% (w/w) by cultivation on standard basal salts medium (BSM) (*Pichia* Fermentation Process Guidelines, Invitrogen) supplemented with a suitable carbon source at a concentration between 30 and 60 g/L, preferably between 40 and 50 g/L. Suitable carbon sources to obtain high *P. pastoris* biomass concentrations include glycerol, methanol and glucose, materials rich in such compounds (e.g. cheese whey, sugar cane molasses, lignocellulosic hydrolysates, glycerol byproduct from the biodiesel industry etc.) or mixtures thereof. Other suitable carbon sources to produce *P. pastoris* biomass include sorbitol, fructose, galactose, xylose, sucrose and lactose, as well as materials rich in such compounds or mixtures thereof.

*P. pastoris* cultivation is performed under batch, fed-batch or continuous mode, with controlled temperature at 28-32° C., controlled pH at 4.5-5.5, and controlled dissolved oxygen concentration (DO) above 10%, preferably above 30%, more preferably above 50%. The pH is controlled by the addition of an alkali solution, preferably ammonium hydroxide that also serves as nitrogen source for cell growth. The DO is controlled by variation of the stirring speed between 200 and 2000 rpm, preferably between 300 and 1000 rpm, variation of the air flow rate between 0.5 and 3.0 vvm (volume of air per volume of reactor per minute), preferably between 1.0 and 2.0 vvm, enrichment with pure oxygen and/or variation of the pressure up to 2.0 bar.

2.2. Procedure for Production of *Pichia pastoris* Biomass with a CGC Content Above 15% (w/w)

In one embodiment, *P. pastoris* biomass is obtained with a CGC content above 15% (w/w) by cultivation on BSM supplemented with glycerol, glucose, fructose, galactose, xylose, sucrose, lactose, mixtures thereof or materials containing such compounds, as carbon source at a concentration between 60 and 180 g/L, preferably between 80 and 120 g/L.

According to the invention, the temperature of cultivation is used to obtain *P. pastoris* biomass with a CGC content above 15% (w/w). High specific cell growth rates (>0.15 h$^{-1}$) are reached by growing *P. pastoris* with temperature controlled at 28-32° C. Outside that temperature range (15-28° C. or 32-50° C.), the specific cell growth rate is lower (<0.15 h$^{-1}$) and changes in the CGC biomass content are induced.

Alternatively, *P. pastoris* is cultivated with controlled temperature at 28-37° C. until the stationary growth phase is reached and, then, the temperature is increased by 5-20° C., preferably by 10-15° C., and the culture is kept at that temperature for a period of time between 2 and 48 hours, preferably between 6 and 24 hours. The heat shock thus imposed to the culture induces changes in the CGC content of *P. pastoris* biomass.

Alternatively, *P. pastoris* is cultivated without temperature control. During exponential cell growth, the temperature gradually increases, thus exposing the culture to increasing temperature values that, consequently, induce changes in the CGC content of *P. pastoris* biomass.

According to the invention, the pH during *P. pastoris* cultivation is also used to control the CGC content of *P. pastoris* biomass. High specific cell growth rates (>0.15 h$^{-1}$) are reached by growing *P. pastoris* with pH controlled at 4.5-5.5. Outside that pH range (2.0-3.5 or 6.5-10.0), the specific cell growth rate is lower (<0.15 h$^{-1}$) and changes in the CGC biomass content are induced.

Alternatively, *P. pastoris* is cultivated with controlled pH at 4.5-5.5 until the stationary growth phase is reached and, then, the pH is increased or lowered by 1.0-3.0, preferably by 2.0-3.0, and the culture is kept at that pH for a period of time between 2 and 48 hours, preferably between 6 and 24 hours. The alkaline or acid shock thus imposed to the culture induces changes in the CGC content of *P. pastoris* biomass.

Alternatively, *P. pastoris* is cultivated without pH control. During exponential cell growth, the pH gradually decreases, thus exposing the culture to an acid environment that, consequently, induces changes in the CGC content of *P. pastoris* biomass.

Control of the CGC content of *P. pastoris* biomass cultivated in BSM with a suitable carbon source is additionally achieved by supplementation of the cultivation medium with glucosamine at a concentration up to 100 mmol/L, preferably between 10-50 mmol/L. The presence of glucosamine stimulates the accumulation of chitin in the cell wall of the yeast, thus enriching the biomass in CGC. Glucosamine is preferably added to the cultivation medium during exponential cell growth phase.

Control of the CGC content of *P. pastoris* biomass cultivated in BSM with a suitable carbon source is additionally achieved by supplementation of the cultivation medium with caffeine at a concentration up to 100 mmol/L, preferably between 10-50 mmol/L. The presence of caffeine affects *P. pastoris* cell growth and causes cell wall damages. Hence, as a defence mechanism against the presence of caffeine, *P. pastoris* increases the amount of chitin in the cell wall, thus enriching the biomass in CGC. Caffeine can be added to the cultivation medium during the exponential cell growth phase or during the stationary growth phase. In order to guaranty that sufficient cell biomass is produced, caffeine is preferably added to the cultivation medium when the biomass has reached a concentration higher than 20 g/L, preferably higher than 50 g/L. Alternatively, caffeine is added at the end of the exponential growth phase or during the stationary growth phase.

Alternatively, changes in the CGC content of *P. pastoris* biomass cultivated in BSM with a suitable carbon source are obtained by supplementing the cultivation medium with a surfactant, such as, for example, sodium dodecyl sulphate (SDS), Triton X100 or polyethylene glycol (PEG), at a concentration up to 1.0% (w/v) preferably between 0.01 and 0.1% (w/v). In the presence of surfactants, *P. pastoris* increases the amount of CGC in the cell wall as a defence mechanism against the cell wall damage caused by the presence of surfactants, thus enriching the biomass in CGC.

Surfactants can be added to the cultivation medium during the exponential cell growth phase or during the stationary growth phase. In order to guaranty that sufficient cell biomass is produced, the surfactant is preferably added to the cultivation medium when the biomass has reached a concentration higher than 20 g/L, preferably higher than 50 g/L.

The CGC content of *P. pastoris* biomass is also affected by the presence of certain salts at concentrations higher than their usual values in BSM. Hence, cultivation of *P. pastoris* in BSM supplemented with calcium, cobalt, copper, iron, magnesium and/or manganese in the form of chloride, sulphate and/or phosphate salts at concentrations up to 200 mmol/L, preferably between 5 and 50 mmol/L, affect the CGC content of *P. pastoris* biomass.

2.3—Procedure for Production of CGC with a Chitin to Glucan Ratio Above 15 to 85 (% mol)

According to the invention, the ratio of chitin to glucan in the CGC is modulated by the cultivation conditions used for *P. pastoris* biomass production. CGC produced by *P. pastoris* commonly has a chitin to glucan ratio up to 15 to 90 (% mol). According to the invention, the chitin to glucan ratio in the CGC is advantageously increased to ratios above 15 to 85 (% mol), preferably above 50 to 50 (% mol), by cultivation of *P. pastoris* in BSM supplemented with glucose, sucrose, lactose, mixtures thereof or materials containing such compounds as carbon sources at concentrations between 40 and 180 g/L, preferably between 60 and 120 g/L.

The chitin to glucan ratio in the CGC is also increased to ratios above 15 to 85 (% mol), preferably above 50 to 50 (% mol), by cultivation of *P. pastoris* in BSM supplemented with caffeine or materials containing caffeine, being the final concentration of caffeine in the BSM up to 100 mmol/L, preferably between 10-50 mmol/L. The presence of caffeine affects *P. pastoris* cell growth and causes cell wall damages. Hence, as a defence mechanism against the presence of caffeine, *P. pastoris* increases the amount of chitin in the cell wall, thus increasing the chitin to glucan ratio in the CGC. Caffeine can be added to the cultivation medium during the exponential cell growth phase or during the stationary growth phase. In order to guaranty that sufficient cell biomass is produced caffeine is preferably added to the cultivation medium when the biomass has reached a concentration higher than 20 g/L, preferably higher than 50 g/L.

The chitin to glucan ratio in the CGC is also increased to ratios above 15 to 85 (% mol), preferably above 50 to 50 (% mol), by cultivation of *P. pastoris* in BSM supplemented with glucosamine at a concentration up to 100 mmol/L, preferably between 10-50 mmol/L. The presence of glucosamine stimulates the accumulation of chitin in the cell wall of *P. pastoris*, thus increasing the chitin to glucan ration in the CGC. Glucosamine is preferably added to the cultivation medium during exponential cell growth phase.

The chitin to glucan ratio in the CGC is also increased to ratios above 15 to 85 (% mol), preferably above 50 to 50 (% mol), by cultivation of *P. pastoris* with pH above 6.5. The alkaline shock thus imposed to the culture induces changes in the chitin to glucan ration of the CGC.

2.4. Extraction of the Natural Biocomposite from *Pichia pastoris* Cell Wall

*P. pastoris* is a methylotrophic yeast, commonly used in the pharmaceutical industry as a host for the production of various recombinant heterologous proteins. Hence, after recovery of the product of such processes, *P. pastoris* biomass is obtained as a byproduct, being available at high quantities and low cost. Therefore, *P. pastoris* resulting as a byproduct from pharmaceutical processes can be advantageously used, according to the method of the invention, to prepare the natural biocomposite as described above.

The natural biocomposite powder prepared from the cell wall of yeast *P. pastoris* comprising 20-95% (w/w) CGC, preferably 40-90% (w/w) and up to 50% (w/w), preferably up to 35% (w/w) mannose-containing polysaccharides, wherein the ratio of chitin to glucan in the CGC is up to 15 to 90 (% mol), preferably higher than 15 to 85 (% mol), more preferably higher than 50 to 50 (% mol), with particle sizes ranging between 5 and 1500 μm, preferably between 30 and 400 μm, apparent bulk densities between 0.05 and 1.0 g/cm$^3$, and sphericity coefficient ranging between 0.20 and 0.95 is prepared by the following method:

a) *P. pastoris* biomass is contacted with an alkaline aqueous solution (NaOH, KOH, $Ca(OH)_2$, $Na_2CO_3$, $K_2CO_3$, $CaCO_3$, $NaHCO_3$ or $KHCO_3$, preferably NaOH or $NaHCO_3$), at a concentration between 0.5 and 2.0 M. The suspension comprises a biomass content between 10 and 15% (w/v).

b) The alkaline biomass suspension is stirred at a temperature between 60-70° C., during 1-5 hours, preferably 2 hours to form a reaction mixture.

c) After cooling the reaction mixture to a temperature between 30 and 45° C., the alkaline insoluble fraction in the reaction mixture is separated from the soluble fraction by centrifugation or filtration.

d) The alkaline insoluble fraction is washed with one or several of the following solvent systems:
   i. Water, being the washings repeated until the pH and the conductivity of the mixture are between 5.0 and 8.0, and below 50 μS/cm, respectively;
   ii. Aqueous saline solution, such as, for example, phosphate buffer saline solution (PBS) (20.45 g/L NaCl; 0.46 g/L KCl; 10.14 g/L $Na_2HPO_4.7H_2O$; 0.54 g/L $KH_2PO_4$, pH 7.2), being the washings repeated until the conductivity of the mixture is between 50 and 200 μS/cm;
   iii. Ethanol (70%, v/v);
   iv. Aqueous solution of an acid, such as, for example, hydrochloric acid (HCl), being the washings repeated until the pH of the mixture is between 5.0 and 8.0;

These washings are intended to improve the removal of the solubilised cell wall components in the extract, namely, proteins (by washing with water and/or PBS solution and/or HCl solution), lipids (by washing with ethanol and/or HCl solution), and salts (by washing with water and/or HCl solution). The appropriate choice of the type of solvent system(s), the number of washings performed and the sequence by which they are performed is used to control the biocomposite's content in proteins, lipids and ashes.

The amount of CGC, mannose-containing polysaccharides, proteins, lipids and ashes in the natural biocomposite are adjusted by controlling the conditions of the method of preparation according to the invention.

2.5. Drying of the Natural Biocomposite Extracted from *Pichia pastoris* Biomass The natural biocomposite prepared from the biomass of the yeast *P. pastoris* according to the invention is dried using one of, but not limited to, the following procedures, known by the person skilled in the art. Various industrial drying equipments such as freeze dryer, fluidized bed dryer, conical dryer, tray dryer, belt dryer, vacuum tray dryer, rotary drier, spray dryer can be used to obtain the dried biocomposite.

In one embodiment of the invention, the wet biocomposite is dried by freezing with liquid nitrogen, followed by lyophilization for 48 hours. The time of lyophilization depends mostly on moisture content of the starting material and is controlled so that the moisture content is below 10%, preferably below 5%.

In another embodiment of the invention, the wet biocomposite is dried in an air drying oven at a temperature between 60 and 80° C., during 12-18 hours.

Advantageously, the biocomposite is spray-dried at temperatures in a range of 120 and 200° C., preferably between 130 and 150° C. One benefit of the spray-drying of the biocomposite is to obtain particles with controlled and homogeneous size, between 15 and 50 μm, preferably between 25 and 35 μm, with a bulk density between 0.25 and 0.95 g/cm$^3$, preferably between 0.45 and 0.75 g/cm$^3$ and presenting essentially a spherical shape, facilitating downstream processing of the obtained powder/granules.

Depending on the drying procedure used, the dried natural biocomposite will be obtained in forms ranging from low density/high volume foams to high density/compact pellets, which are used to modulate the physical properties.

It is an advantage of the present invention to produce a dry biocomposite that can be further processed and milled according the necessity of the pharmaceutical industry, looking for high processability.

2.6. Milling Procedure for Preparation of the Natural Biocomposite Powder

The natural biocomposite powder of this invention is prepared by any method known in the prior art for the production of powders or granules, such as fluidized bed granulation, high shear granulation, spray drying or wet granulation. Preferably, the dried biocomposite is milled and granulated by any industrial fragmentation and disintegrating equipment used to obtain granules and known by the people skilled in the art, such as hammer, roller, knife, blade, or disks. The granulators used in this process can be low shear, like for instance fluid-bed granulator, medium shear or high shear granulators.

In one embodiment of the invention, the natural biocomposite dried at temperatures between 40 and 100° C. is milled by passing through a comminuting mill equipped with knife impact rotor and a sieve ranging from 0.25 mm to 10 mm in the output, preferably a sieve ranging from 0.25 to 1.0 mm in the output. The material obtained is processed a second time in the same equipment with a sieve ranging from 0.25 mm to 5 mm, preferably a sieve ranging from 0.25 mm to 0.5 mm. The resulting granulate is passed through an oscillating and rotating sieve mill with a sieve ranging from 0.0125 to 2.5 mm.

Alternatively, the dried natural biocomposite can be milled by passing through a Cone Mill, equipped with a conical or V rotor, and a sieve ranging from 0.25 mm to 10 mm in the output, preferably a sieve ranging from 0.25 to 1.0 mm in the output. The rotor speeds used can range from 500 rpm to 5000 rpm.

In another alternative, the natural biocomposite can be milled by passing through a Ball Mill. The rotor speeds used can range from 500 rpm to 1500 rpm.

In another alternative, the natural biocomposite can be milled by passing through a Multi Mill. The rotor speeds used can range from 500 rpm to 5000 rpm.

Another option is that the natural biocomposite dried by freeze drying or by spray drying or fluidized bed drying or by conical dryer, is passed through a roller compactor also known as a chilsonator, for instance like the chilsonator IR520, once or twice, or as many times as considered sufficient, to obtain the powder of interest.

In the present invention, the biocomposite powder is prepared in such a way that it has a particle size ranging between 5 μm and 1500 μm, preferably between 30 and 400 μm.

The powder obtained by any of the methods described above, is calibrated by any of the calibration methods used by the person skilled in the art, such as screening on successive sieves followed by gravimetric measurements. For instance, the particles can be calibrated in an oscillating and rotating sieve mill equipped with a sieve ranging from 0.05 mm to 1.5 mm. It is preferred that at least 85% of the particles should have a particle size between 0.5 μm 1500 μm, preferably in the range from 200 μm and 500 μm. It is also preferred that fines (i.e. particles with a size below 90 μm) are residual in order to facilitate future compression of the powder into tablets, preferably below 1%. In a preferred embodiment, 90% of the particles have a size below 355 μm, 50% have a size below 250 μm and less than 10% have a size below 90 μm.

The natural biocomposite powder of the present invention is characterized by particles with the minimum possible porosity, preferably less than 2.5%, which is controlled by adjusting the parameters of the drying process, such as drying speed, time and temperature. The particles shape may be spherical or cylindrical or even laminated, depending on the combination of procedures performed previously, but the final shape will preferably be spherical.

Following European Pharmacopeia 2.9.15 (Apparent volume), the apparent bulk density of the obtained particles is in the range 0.05-1.0 g/cm$^3$, preferably in the range 0.2-1.0 g/cm$^3$, more preferably in the range 0.5-1.0 g/cm$^3$. Packed density of the biocomposite powder obtained is comprised between 0.4 and 1.7 g/cm$^3$, preferably between 0.5 and 1.5 g/cm$^3$.

Parameters such as angle of repose, Carr index, Hausner ratio and flow time are used by the people skilled in the art to characterize the flow properties of a powder. It is an advantage of the present invention to produce a biocomposite powder presenting an angle of repose between 20 and 40°, preferably between 25 and 30°.

In another embodiment, the powder presents a Carr index between 10% and 25%, preferably between 15% and 20%. It is another advantage of the invention to obtain a powder with a Hausner ratio below 1 and a flow time below 5 s, according to the classification in the European Pharmacopoeia 2.9.36 (Powder flow).

It has been established that the pharmaceutical excipient according to the present invention provides properties of improved flowability, high compatibility and compressibility, as well as fast disintegration. By better flowability, it is meant that the powder presents flow time below 5 s, better than microcrystalline cellulose, one of the most common widely used excipient available in the market. Obviously, this is one advantage of the present invention, as the feeding rates of the material are critical for attaining the final objective.

By improved compressibility, it is meant that a lower compression force has to be used to obtain tablets with acceptable hardness and disintegration time. For instance, a 15 kN compression force is sufficient to obtain satisfactory tablets with a hardness of 7 Kgf with the described biocomposite of the invention.

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

EXAMPLES

Example 1: Production of *Pichia pastoris* Biomass in a Fed-Batch Bioreactor Cultivation with Exponential Feeding

*P. pastoris* strain DSM 70877 was cultivated in standard basal salts medium (BSM) (*Pichia* Fermentation Process Guidelines, Invitrogen) with the following composition (per liter): $H_3PO_4$ 85%, 26.7 mL; $CaSO_4$, 0.93 g; $K_2SO_4$, 18.2 g; $MgSO_4$, $7H_2O$, 14.9 g; KOH, 4.13 g; Antifoam A (Sigma), 0.75 mL and 4.35 mL of a trace elements solution (PTM). PTM solution had the following composition (per liter): $CuSO_4.5H_2O$, 6 g; NaI, 0.08 g; $MnSO_4.H_2O$, 3 g; $Na_2MoO_4.2H_2O$, 0.2 g; $H_3BO_3$, 0.02 g; $CoCl_2.6H_2O$, 0.5 g; $ZnCl_2$, 20 g; $Fe_2SO_4.7H_2O$, 65 g; biotin, 0.2 g and $H_2SO_4$, 5 mL. The PTM solution was filter sterilized separately and added to the BSM medium after its sterilization at 121° C. for min. BSM was supplemented with glycerol, sterilized at 121° C. for 30 min, to give a concentration of 40 g/L.

The inoculum was prepared by incubating the culture in BSM medium, containing glycerol (40 g/L), in shake flasks for 2 days at 30° C., in an incubator shaker (250 rpm). This pre-inoculum was used to inoculate a 250 mL shake flask at 10% (v/v), which was grown for 3 days at 30° C. and 250 rpm.

The cultivation was carried out in a 2 L bioreactor (BioStat B-plus, Sartorius) with an initial working volume of 1.4 L. The bioreactor was operated with controlled temperature and pH of 30° C.±0.1 and 5.0±0.05, respectively. pH was controlled by the addition of 25% ammonium hydroxide solution that served also as the nitrogen source. The DO concentration was controlled above 30% by the automatic variation of the stirring rate (between 300 and 1000 rpm) and enrichment of the air stream with pure oxygen. An initial batch phase was performed during 26 hours. Fed-batch mode was initiated when a decrease in the oxygen consumption rate was observed, by supplying the bioreactor with glycerol supplemented with 24 mL of trace elements PTM solution per liter of glycerol, using an exponential feeding rate, $F=F_0\times e^{\mu t}$, with F being the feeding rate in g/h, $F_0$ the initial feeding rate (5.6 g/h), and μ the desired specific growth rate, 0.16 $h^{-1}$.

During the initial batch cultivation (26 hours), *P. pastoris* cells grew at a maximum specific growth rate of 0.17 $h^{-1}$ and g/L of biomass were reached, from a starting glycerol concentration of 40 g/L. This corresponds to a yield of 0.55 g biomass per g of glycerol, similar to published results of *P. pastoris* growth on pure glycerol (0.55 g/g, by Oliveira et al., 2005) or crude glycerol (0.57 g/g, by Celik et al., 2008).

After 26 hours, when glycerol was depleted, as indicated by a drop in stirring rate (corresponding to a drop in oxygen consumption rate), the fed-batch phase with exponential feeding was initiated, resulting in an immediate increase in the oxygen consumption rate. Biomass concentration reached 104 g/L after 41 hours culture. Biomass yield increased slightly to 0.63 g biomass per g consumed glycerol during the fed-batch phase (close to 0.7 g/g found by Jahic et al., 2002). Final cell concentration was in the range of results obtained by other authors with pure glycerol (75-120 g/L) (Chauhan et al., 1999; Oliveira et al., 2005).

Example 2: Production of *Pichia pastoris* Biomass in a Batch Bioreactor Cultivation

*P. pastoris* strain DSM 70877 was cultivated in BSM with the composition described in Example 1. BSM was supplemented with glycerol, sterilized at 121° C. for 30 min, to give a concentration of 60 g/L.

The inoculum was prepared by incubating the culture in BSM medium, as described in Example 1, except for the glycerol concentration that was 60 g/L.

The cultivation was carried out in a 5 L bioreactor (BioStat B-plus, Sartorius) with an initial working volume of 3.0 L. The bioreactor was operated with controlled temperature and pH of 30° C.±0.1 and 5.0±0.05, respectively. pH was controlled by the addition of 25% ammonium hydroxide solution that served also as the nitrogen source. The DO concentration was controlled above 50% by the automatic variation of the stirring rate (between 300 and 2000 rpm) and enrichment of the air stream with pure oxygen.

The batch cultivation run took 32 hours until the culture attained the stationary growth phase by depletion of the carbon source. During the exponential growth phase, *P. pastoris* cells grew at a specific growth rate of 0.18 $h^{-1}$. At the end of the run, 42 g/L of biomass were reached, from a starting glycerol concentration of 54 g/L. This corresponds to a yield of 0.79 g biomass per g of glycerol, which was higher than the value obtained in Example 1.

Example 3: Extraction of Natural Biocomposite from *Pichia pastoris* Biomass Using Alkaline Treatment with NaOH 1M and Washing of the Alkaline Insoluble Fraction with PBS Solution The cultivation broth (200 mL) of *P. pastoris* produced as described in example 1 was centrifuged (10 000 g, for 15 minutes) and the supernatant was discarded. The wet cell pellet was treated with NaOH 1M (200 mL) at 65° C., for 2 h. The suspension had a biomass content of 10.4% (w/v) on a dry basis.

The reaction mixture was centrifuged (10 000 g, for 15 minutes) to separate the alkaline insoluble fraction from the alkaline soluble fraction that was discarded.

The alkaline insoluble fraction was washed twice with 200 mL of deionised water to remove alkali soluble components. Then, it was sequentially subjected to two washes with the same volume of phosphate buffer saline solution (PBS) (20.45 g/L NaCl; 0.46 g/L KCl; 10.14 g/L $Na_2HPO_4.7H_2O$; 0.54 g/L $KH_2PO_4$, pH 7.2) in order to improve elimination of residual proteins, and one wash with ethanol (70%, w/v) for the removal of lipids. A final wash with deionised water was performed in order to remove ethanol and residual salts. The resulting natural biocomposite was lyophilized (48 h).

For the determination of the composition of the natural biocomposite in sugars, two acid hydrolysis procedures were performed: trifluoroacetic acid (TFA) was used to hydrolyse mannose-containing polysaccharides and the glucan moiety of the CGC, while a stronger acid (HCl) was necessary for the quantification of the chitin fraction in the CGC. For the TFA hydrolysis, freeze-dried biocomposite samples (~5 mg) were resuspended in deionised water (5 mL) and 0.1 mL TFA 99% were added. The hydrolysis was performed at 120° C., for 2 hours. For the HCl hydrolysis, the freeze-dried biocomposite samples (~5 mg) were resuspended in HCl 12N (7.5 mL). The hydrolysis was performed at 120° C., for 5 hours. Both hydrolysates were used for the quantification of the constituent monosaccharides by liquid chromatography (HPLC), using a CarboPac PA10 column (Dionex), equipped with an amperometric detector. The analysis was performed at 30° C., with sodium hydroxide (NaOH 4 mM) as eluent, at a flow rate of 0.9 mL/min. Glucose (Sigma), mannose (Sigma) and glucosamine (Sigma) were used as standards, being subjected to the same hydrolysis procedures as the polymer samples.

For the determination of the biocomposite's content in proteins, freeze-dried samples were hydrolyzed with 2 M NaOH (7 mg:1 ml) in sealed vials, at 120° C., for 15 min. The supernatant obtained by centrifugation (10 000 g, 10 minutes) was used for the protein assay, according to the modified Lowry method. A 1-mL aliquot of alkaline copper sulphate reagent was added to 1 mL of the supernatant (diluted when necessary) and allowed to stand for 10 min at room temperature. A 3-mL aliquot of diluted Folin-Ciocalteu reagent was added, and incubated for 30 min at room temperature. Absorbance was read at 750 nm. Bovine serum albumin (BSA, Sigma) was used as standard.

The ash content of the biocomposite was determined by subjecting freeze-dried samples to pyrolysis at a temperature of 550° C., for 48 hours.

Differential Scanning Calorimetry (DSC) analyses of the freeze-dried biocomposite were conducted with a Setaram Calorimeter (model DSC 131, France) under a protective nitrogen gas atmosphere. Accurately weighed dried material was placed in an aluminium cup and hermetically sealed. The measurements were carried out from 25 to 450° C. under nitrogen at a scanning rate of 10° C./min.

The natural biocomposite prepared from *P. pastoris* biomass using the procedure described was obtained as a slightly yellow powder with a water content of about 6% (w/w). It represented 23.6% of the cell's dry weight. As determined by the compositional analysis performed with the TFA and HCl hydrolysates, the biocomposite was composed of 42% (w/w) CGC and 28% (w/w) mannose containing polysaccharides. The glucose (35%, w/w) and glucosamine (7%, w/w) contents of CGC correspond to a chitin to glucan ratio of 16 to 84 (% mol). Moreover, the biocomposite obtained using the procedure described in the example also had a total protein content of 9.5 wt %, as well as an ash content of 15.0 wt %.

The thermal properties of the natural biocomposite prepared from *P. pastoris* showed that it presented a broad endothermic peak around 50-100° C., which can be attributed to the evaporation of the water bound to the biocomposite (FIG. 1). The strong endothermic peak suggests that the biocomposite presents a high water holding capacity. The biocomposite showed two decomposition exothermic peaks at 205.18 and 288.38° C. The presence of the two exothermic decomposition peaks is indicative of the presence of different polymers, probably the mixture of CGC and mannose-containing polysaccharides. Furthermore, the very low amount of peak enthalpy for the biocomposite would suggest a biomaterial with very low crystallinity.

Example 4: Extraction of Natural Biocomposite from *Pichia pastoris* Biomass Using Alkaline Treatment with NaOH 5M and Washing of the Alkaline Insoluble Fraction with HCl 1M Solution The cultivation broth (200 mL) of *P. pastoris* produced as described in example 1 was centrifuged (10 000 g, for 15 minutes) and the supernatant was discarded. The wet cell pellet was treated with NaOH 5M (200 mL) at 60° C., for 2 h. The suspension had a biomass content of 10.4% (w/v) on a dry basis.

The alkaline soluble fraction was discarded from the alkaline-insoluble fraction by centrifugation (10 000 g, for 15 minutes).

The alkaline insoluble fraction was resuspended in 200 mL of deionised water and the pH of the suspension was adjusted to 7.0 by the addition of HCl 12 N. Then, it was repeatedly washed with deionised water (8×200 mL). The suspension pH and conductivity were monitored during the washing procedure, which ended when the pH and conductivity were 6.3 and 15 μS, respectively. The resulting natural biocomposite was lyophilized for 48 h.

The composition of the natural biocomposite prepared with this procedure was determined as described in Example 3. DSC was also performed as described in Example 3.

The natural biocomposite prepared from *P. pastoris* biomass using the procedure described in the example was obtained as a pale powder with a water content of below 5% (w/w). It represented 12.4% of the cell's dry weight. As determined by the compositional analysis performed with the TFA and HCl hydrolysates, the biocomposite was composed of 89% (w/w) CGC and only 1.7% (w/w) mannose containing polysaccharides. The glucose (71%, w/w) and glucosamine (18%, w/w) contents of CGC correspond to a chitin to glucan ratio of 20 to 80 (% mol). Moreover, it also had a total protein content of 3.0 wt % and no ashes have been detected in the sample.

The thermal properties of the natural biocomposite prepared from *P. pastoris* showed that it also presented an endothermic peak around 50-100° C., which can be attributed to the evaporation of the water bound to the biocomposite (FIG. 1). The weaker endothermic peak in comparison with the biocomposite obtained in example 3 suggests that it presents a lower water holding capacity. The biocomposite showed a single strong decomposition endothermic peak at 320° C., which suggests a biomaterial with higher crystallinity than the material obtained in Example 3.

Example 5: Effect of *Pichia pastoris* Cultivation Conditions on CGC Content in the Biomass and on the Chitin to Glucan Ratio of the CGC

*P. pastoris* strain DSM 70877 was cultivated in BSM with the composition described in Example 1. The cultivation assays were carried out in batch shake flasks, in an incubator shaker (250 rpm), at 30° C., for 96 hours, except the assays wherein the effect of the initial pH was studied that took 48 hours. The pH was not controlled in any assay, but it was monitored throughout the runs. Several cultivation conditions were tested, as shown in Table 1. At the end of the assays, the natural biocomposite was extracted from *P. pastoris* biomass using the procedure described in example 4.

TABLE 1

*Pichia pastoris* batch shake flask assays, under different cultivation conditions

| Assay | Conditions | Initial pH | Final pH | CDW (g/L) | CGC (%, w/w) | Chitin:glucan ratio (% mol) |
|---|---|---|---|---|---|---|
| 1 | Glycerol 40 g/L | 4.96 | 3.97 | 9.23 | 15 | 14:86 |
| 2 | Glycerol 50 g/L | 4.60 | 3.26 | 9.74 | 13 | 10:90 |
| 3 | Glycerol 60 g/L | 4.65 | 2.28 | 10.26 | 22 | 13:87 |
| 4 | Glycerol 100 g/L | 4.57 | 2.36 | 6.22 | 23 | 13:87 |
| 5 | Sorbitol 30 g/L | 4.39 | 2.46 | 8.98 | 12 | 9:91 |
| 6 | Glucose 40 g/L | 5.04 | 3.55 | 5.48 | 12 | 68:32 |
| 7 | Galactose 30 g/L | 5.09 | 4.85 | 2.81 | 14 | 15:85 |
| 8 | Lactose 40 g/L | 4.87 | 4.64 | 2.53 | 21 | 19:81 |
| 9 | Sucrose 40 g/L | 5.07 | 4.61 | 3.64 | 23 | 19:81 |
| 10 | Glycerol 40 g/L + Glucosamine 12 mM | 5.05 | 3.64 | 7.99 | 17 | 23:77 |
| 11 | Glycerol 40 g/L + Caffeine 12 mM | 4.64 | 3.35 | 3.42 | 25 | 19:81 |
| 12 | Glycerol 40 g/L + $MgSO_4$ 140 mM | 4.35 | 3.23 | 6.95 | 27 | 13:87 |
| 13 | Glycerol 40 g/L + $MnCl_2$ 200 mM | 3.90 | 3.12 | 9.29 | 16 | 11:89 |
| 14 | Glycerol 40 g/L + $CaSO_4$ 200 mM | 4.65 | 2.41 | 12.43 | 24 | 15:85 |
| 15 | Glycerol 40 g/L + $CaCl_2$ 200 mM | 4.25 | 3.06 | 4.36 | 23 | 10:90 |
| 16 | Glycerol 40 g/L (48 hours) | 2.16 | 2.27 | 1.69 | 10 | 10:90 |
| | | 3.13 | 2.60 | 3.01 | 10 | 10:90 |
| | | 3.93 | 2.80 | 7.76 | 11 | 10:90 |
| | | 4.64 | 3.36 | 8.13 | 12 | 12:88 |
| | | 5.91 | 5.38 | 5.07 | 13 | 15:85 |
| | | 6.88 | 6.14 | 5.96 | 14 | 16:84 |
| | | 7.34 | 6.41 | 7.72 | 19 | 18:82 |
| | | 7.54 | 6.54 | 5.61 | 31 | 17:83 |
| | | 8.36 | 6.80 | 4.36 | 41 | 17:83 |
| | | 9.58 | 7.43 | 2.11 | 68 | 16:84 |
| | | 10.67 | 9.49 | 0 | — | — |

Under the batch conditions of these assays, it was observed that cell growth was favored (CDW>8.00 g/L) by cultivation with BSM supplemented with glycerol at a concentration between 40 and 60 g/L, being reduced for a glycerol concentration of 100 g/L. Sorbitol was also a good carbon source for growth. Supplementation with $MnCl_2$ or $CaSO_4$ also resulted in increased cell growth. On the other hand, the conditions that considerably depressed cell growth (CDW<4.00 g/L) were the use of galactose (30 g/L), lactose (40 g/L) or sucrose (40 g/L) as carbon sources, supplementation with caffeine, initial pH below 3.0 or above 8.5.

The highest CGC content (>15%, w/w) in *P. pastoris* biomass was obtained for cultivation with BSM supplemented with glycerol as carbon source at concentrations 60 g/L. Although the use of lactose and sucrose as carbon sources led to reduced cell growth, the biomass had an increased content of CGC (21-23%, w/w). Supplementation of BSM medium with caffeine and glucosamine also resulted in high CGC content (25 and 17% (w/w), respectively). Supplementation of BSM medium with $MgSO_4$, $MnCl_2$, $CaSO_4$ or $CaCl_2$ at concentrations between 140 and 200 mmol/L also resulted in high CGC content (between 16 and 27%, w/w). Initial pH above 7.0 also considerably increased CGC content in *P. pastoris* biomass (above 19%, w/w).

Increased chitin to glucan ratios (above 15 to 85, % mol) were obtained for cultivation using glucose, lactose or sucrose as carbon sources, supplementation with caffeine or glucosamine, and initial pH between 6.0 and 10.0.

Example 6: Drying and Milling the Natural Biocomposite

The natural biocomposite obtained by the procedure described in Example 3 was mixed with deionised water (31 g of lyophilized biocomposite+900 mL of deionised water) to produce a thick homogeneous slurry. The biocomposite slurry was spread in anti-adherent trays (around 0.5 mm thick layers) and placed in an oven at 70° C., for 16 hours.

The dried natural biocomposite (31.231 g) was passed through a Comminuting mill with a 1 mm sieve and after through an oscillating and rotation mill (Erweka pilot-plant device) with a 0.5 mm aperture sieve in to obtain reduced particle size high density granules. The calibration was made by passing the powder through a 0.75 mm sieve, in the oscillating and rotation milling device, through a 0.50 mm sieve and, finally, through a 0.35 mm sieve in the same equipment. The granulometric distribution of the powder thus obtained was as follows (Table 2):

TABLE 2

Granulometric distribution of the powder obtained from the biocomposite dried at 70° C., after milling and calibration

| Size (μm) | Proportion (%, w/w) |
|---|---|
| >355 | 8.73 |
| 250-355 | 43.45 |
| 180-250 | 17.77 |
| 125-180 | 15.12 |
| 90-125 | 7.32 |
| 0-90 | 7.03 |

The average apparent density was 0.64 g/cm and the tapped density was 0.71 g/$cm^3$.

Example 7: Preparation of Tablets Using the Natural Biocomposite Powder Prepared from *Pichia pastoris* Biomass as Excipient The biocomposite powder obtained as described in Example 5 was used as a binder/filler in typical current direct compression formulae in a percentage range of 20 to 85% as follows (Table 3):

TABLE 3

Current direct compression formulae used to produce tablets with the natural biocomposite prepared from *P. pastoris* biomass

| Substance | % | mg/tablet |
|---|---|---|
| Biocomposite | 50.000 | 50.00 |
| Lactose monohydrate | 30.000 | 30.00 |
| Colloidal silicon dioxide | 6.667 | 6.67 |
| Sodium starch glycolate | 8.333 | 8.33 |
| Magnesium stearate | 5.000 | 5.00 |
| Total | 100.000 | 100.00 |

The rheological characterisation of the final powder mixture was first analysed visually. Afterwards the angle of repose was determined and the obtained Carr Index value was 9.8, which indicates a powder with very good flowability (below 12). Tablet compression trials were performed in a Piccola Model B-10 machine, a Hi-Tech Rotary Tablet Press for Research & Development from RIVA, using round concave punches with 7 mm diameter. The tablets obtained had a theoretical weigh of 100 mg (95-105 mg), 7.5 Kgf of hardness, less than 1% of friability and less than 5 minutes of disintegration time in water at 37° C.

REFERENCES

Celik E, Ozbay N, Oktar N, Calik P (2008) Ind Engineer Chem Res 47(9), 2985-2990.

Oliveira R, Clemente J J, Cunha A E, Carrondo M J T (2005) J Biotechnol 116(1), 35-50

Jahic M, Rotticci-Mulder J C, Martinelle M, Hult K, Enfors S O (2002) Bioprocess Biosyst Eng 24, 385-393.

Chauhan A K, Arora D, Khanna N (1999) Process Biochemistry 34(2), 139-145.

What is claimed is:

1. A biocomposite powder comprising 40-95% (w/w) chitin-glucan complex (CGC), and up to 25% (w/w) mannose-containing polysaccharides, wherein the size of particles of the biocomposite powder range between 5 and 1500 μm, and wherein the apparent bulk density of the biocomposite powder is between 0.05 and 1.0 g/cm$^3$.

2. The biocomposite powder of claim 1, wherein the size of particles of the composite powder range between 30 and 400 μm.

3. The biocomposite powder of claim 1, wherein the apparent bulk density of the biocomposite powder is between 0.5 and 1.0 g/cm$^3$.

4. The biocomposite powder of claim 1, wherein the granulometric distribution of the biocomposite powder is such that 90% of the particles have a size below 355 μm, 50% have a size below 250 μm and less than 10% have a size below 90 μm.

5. The biocomposite powder of claim 1, wherein the ratio of chitin to glucan in the CGC is up to 15 to 90 (% mol).

6. The biocomposite powder of claim 1, wherein the biocomposite powder is an extract of the biomass of the yeast *Pichia pastoris*.

7. The biocomposite powder of claim 1, wherein the ratio of chitin to glucan in the CGC is higher than 15 to 85 (% mol).

8. The biocomposite powder of claim 1, wherein the ratio of chitin to glucan in the CGC is higher than 50 to 50 (% mol).

9. A method for preparing the biocomposite powder of claim 1, characterized by the following sequential steps:

a) contacting *P. pastoris* biomass with an alkaline aqueous solution, at a concentration between 0.5 and 5.0 M, wherein the biomass is in suspension, preferably at a concentration between 10 and 15% (w/v);

b) stirring the alkaline biomass suspension at a temperature between 60-90° C. for a period of 1-5 hours to form a reaction mixture;

c) cooling the reaction mixture to a temperature between 30 and 45° C., and after cooling, separating the alkaline insoluble fraction in the reaction mixture from the soluble fraction by centrifugation or filtration;

d) washing the alkaline insoluble fraction with one or several of the following solvent systems to form a slurry:

i. water, ii. aqueous saline solution, iii. ethanol (70%, v/v), or iv. aqueous solution of an acid;

e) drying the slurry using one of the following procedures:

i. freezing with liquid nitrogen, followed by lyophilization;

ii. drying in an oven at a temperature between 60 and 80° C., for 12-18 hours;

iii. spray-drying at a temperature of between 120 and 200° C., for a period of time between 1 and 10 seconds; or iv. fluidized bed drying with inlet air between 70° C. and 90° C.;

f) milling the dried material to obtain a powder by passing it one or more times through a Comminuting Mill, a Cone Mill, a Ball Mill, a Multi Mill or a Roller Compactor, equipped with sieves ranging from 0.25 to 10 mm in the output, operated with rotor speeds between 500 and 5000 rpm; and g) calibrating the powder by passing it one or more times through an oscillating and rotating sieve mill equipped with sieves ranging from 0.05 to 1.5 mm.

10. The method of claim 9, wherein the *Pichia pastoris* biomass is obtained by cultivation in BSM supplemented with glycerol, glucose, fructose, galactose, xylose, sucrose, lactose, mixtures thereof or materials containing such compounds as carbon sources at concentrations between 80 and 120 g/L.

11. The method of claim 9, wherein *Pichia pastoris* biomass is obtained by cultivation without temperature control.

12. The method of claim 9, wherein *Pichia pastoris* biomass is obtained by cultivation with controlled temperature at 28-32° C. until the stationary growth phase is reached and then increasing the temperature by 5-20° C. during 2-48 hours.

13. The method of claim 9, wherein the *Pichia pastoris* biomass is obtained by cultivation with controlled temperature at 28-32° C. until the stationary growth phase is reached and then increasing the temperature by 10-15° C., during 2-48 hours.

14. The method of claim 9, wherein the *Pichia pastoris* biomass is obtained by cultivation without pH control.

15. The method of claim 9, wherein the *Pichia pastoris* biomass is obtained by cultivation in BSM supplemented with caffeine or materials containing caffeine, wherein the final concentration of caffeine in BSM is up to 100 mmol/L.

16. The method of claim 9, wherein the *Pichia pastoris* biomass is obtained by cultivation in BSM supplemented with glucosamine at a concentration between 10-50 mmol/L.

* * * * *